(12) United States Patent
Blanchard-Bregeon et al.

(10) Patent No.: US 6,387,936 B1
(45) Date of Patent: May 14, 2002

(54) COMBINATIONS OF RILUZOLE AND LEVODOPA FOR THE TREATMENT OF PARKINSON'S DISEASE

(75) Inventors: Véronique Blanchard-Bregeon; Assunta Imperato, both of Paris; Saliha Moussaoui, Fontenay Sous Bois; Marie-Carmen Obinu, Paris; Michel Reibaud, Creteil, all of (FR)

(73) Assignee: Aventis Pharma S.A., Anthony (FR)

(*) Notice: Subject to any disclaimer, the term of this patent is extended or adjusted under 35 U.S.C. 154(b) by 0 days.

(21) Appl. No.: 09/694,860

(22) Filed: Oct. 24, 2000

Related U.S. Application Data

(63) Continuation of application No. PCT/FR99/00953, filed on Apr. 22, 1999.

(30) Foreign Application Priority Data

Apr. 24, 1998 (FR) .............................................. 98/05153

(51) Int. Cl.⁷ ............................................ A61K 31/425
(52) U.S. Cl. ....................................................... 514/367
(58) Field of Search ......................................... 514/367

(56) References Cited

FOREIGN PATENT DOCUMENTS

WO           9415601           7/1994           ................. 514/367

OTHER PUBLICATIONS

Rascol O. et al.: 'Pharmacologie Clinique Des Dyskinesies Induites Par la L–Dopa Chez les Malades Parkinsoniens' Therapie [Clinical Pharmacology of Dyskinesias Induced by L–Dopa in Parkinson's Sufferers Therapy] (Therapie0, 53/1 (43–48), Feb. 1998.

Starr M.S.: 'Antiparkinson actions of glutamate antagonists—alone and with L–Dopa: A review of evidence and suggestions for possible mechanisms' Journal of Neural Transmission—Parkinson's Disease and Dementia Section (J. Neural Transm. Parkinson's Dis. Dementia Sect.), 10/2–3 (141–185, Dec. 20, 1995).

Montastruc J.–L. et al: 'New directions in the drug treatment of Parkinson's disease' Drugs and Aging (Drugs Aging), 9/3 (169–184), 1996).

Starr M.S. et al: 'Stimulation of basal and L–Dopa–induced motor activity by glutamate antagonists in animal models of Parkinson's disease' Neuroscience and Biobehavioral Reviews (Neurosci. Biobehav. Rev.), 21/4 (437–446), 1997).

A. Ekesbo et al., Neuroreport, 8, 2567–2570, 1997.

R.K.B. Pearce et al., Movement Disorders, vol. 10, No. 6, 731–740, 1995.

J.G. Nutt, Neurology, 40, 340–345, 1990.

*Primary Examiner*—James H. Reamer
(74) *Attorney, Agent, or Firm*—Balaram Gupta

(57) ABSTRACT

The invention concerns a combination of levodopa and riluzole or a pharmaceutically acceptable salt of said compound and the use of said combination for treating Parkinson Disease.

20 Claims, 3 Drawing Sheets

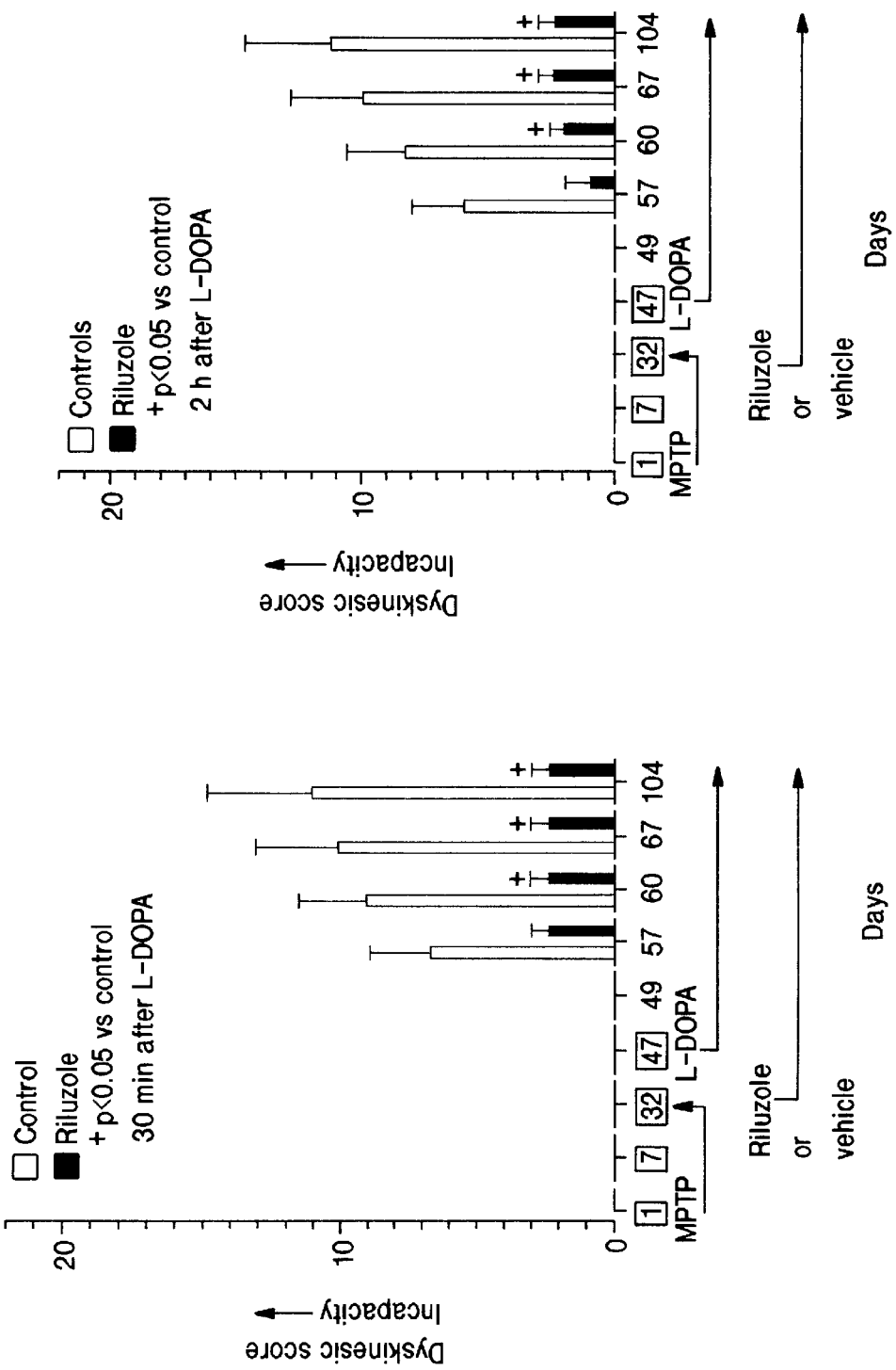

COMBINATIONS OF RILUZOLE AND LEVODOPA FOR THE TREATMENT OF PARKINSON'S DISEASE

This application is a continuation of International application number: PCT/FR99/00953, filed Apr. 22, 1999; which claims the benefit of priority to French Patent Application No. 98/05,153, filing date Apr. 24, 1998.

The present invention relates to a combination of L-DOPA and riluzole or a pharmaceutically acceptable salt of this compound and the use of this combination for the treatment of Parkinson's disease.

Parkinson's disease is connected with destruction of the locus niger (substantia nigra) which results in degeneration of the dopaminergic neurons of the nigrostriatial tract and therefore a massive decrease in the levels of dopamine in the striatum. To compensate the depletion of dopamine which is consequent to the degeneration of dopaminergic neurons of the nigrostriatial tract in parkinsonian patients, L-DOPA, (3-(3,4-dihydroxyphenyl)-L-alanine) or levodopa, which is converted into dopamine by dopa decarboxylase, is used as a symptomatic treatment of Parkinson's disease. After oral administration, the L-DOPA is massively decarboxylated at the peripheral level into dopamine, which does not cross the blood-brain barrier; this is why it is generally administered in combination with a decarboxylase inhibitor such as benserazide or carbidopa. These decarboxylase inhibitors actually allow the dose of L-DOPA to be reduced by approximately 5 (Rondot P. et al., Pharmacologie Clinique, bases de la thérapeutique [*Clinical Pharmacology, Therapeutic bases*], published by J.-P. Giroud, G. Mathé and G. Meyniel, 2nd edition, Expansion Scientifique Frangaise, 1988, page 1127).

In patients suffering from Parkinson's disease, L-DOPA reduces the severity of symptoms such as bradykinesia (poverty of movements), muscular rigidity and trembling. However, chronic treatment with L-DOPA leads, in 30% to 80% of parkinsonian patients, to secondary effects and, in particular, to dyskinesias (J. G. Nutt, Neurology, 40, 340–345, 1990).

These dyskinesias are also reproduced by a chronic treatment with L-DOPA in marmosets rendered parkinsonian following an injection of MPTP (1-methyl-4-phenyl-1,2,3,6-tetrahydropyridine), a toxin which destroys the dopaminergic neurons of the nigrostriatial path (R. K. B. Pearce et al., Movement Disorders, vol. 10, No. 6, 731–740, 1995; A. Ekesbo et al., Neuroreport, 8, 2567–2570, 1997).

Riluzole (2-amino-6-trifluoromethoxybenzo-thiazole) is marketed for the treatment of amyotrophic lateral sclerosis. It is also known for its neuroprotective effect in the treatment of Parkinson's disease (WO94/15601).

It has now been found that the combination of riluzole or one of its pharmaceutically acceptable salts and of L-DOPA improves the locomotory activity of parkinsonian marmosets and, in addition, prevents the dyskinesias induced by L-DOPA.

The activity of the riluzole and L-DOPA combination is determined according to the following protocol: 6 adult marmosets (*Callithrix jacchus*, Harlan UK) aged 25 months and weighing between 300 and 350 g are accommodated in stainless steel cages (50 cm in width×20 cm in depth×23 cm in height) with wire netting doors, these cages being connected to smaller cages (28×20×23 cm) in which the marmosets can sleep. The animals are accommodated in a controlled environment: temperature of 24±2° C., humidity of 55%, with a day-night cycle of 12 hours. The marmosets have free access to water and have available each day 35 g of food rich in carbohydrates, proteins and vitamins mixed with water, milk and sugar and also fresh fruit.

All the animals receive 3 injections of 2 mg/kg of MPTP by the subcutaneous route, on days 1, 7 and 32. On day 32, the animals are divided into 2 groups. Group 1 (control group) receives 2 oral administrations of 10% sucrose and group 2 (treated group) receives 2 oral administrations of riluzole (10 mg/kg) suspended in 0.5% methylcellulose, each day to day 104. On day 47, the two groups of animals receive an oral administration of L-DOPA (Modopar® 125 dispersible Roche (L-DOPA (25 mg)+benserazide (6.25 mg)). on day 48, they receive 2 oral administrations and from day 49 to day 104 they receive 3 oral administrations of L-DOPA each day.

LOCOMOTORY ACTIVITY

The locomotory activity is determined by placing the animals in test cages (50 cm×83 cm×77 cm) which are equipped with 3 perches onto which the animals can jump as well as a Plexiglas door in front of which is placed a camera. This camera is connected to an image analyser system (Vigie Primates, View Point$^R$, which is capable of calculating the quantity of movements of 8 marmosets, simultaneously and independently for the duration of the test. The principle of this system is to quantify the movements of the animals in the cage in a determined time window (5s). The image is digitalized with a 800×600 definition with 256 levels of grey and the changes in pixels from one image to another are counted. This allows the locomotory activity to be classified into small, medium or large movements. Each class of movements is analysed every 10 minutes for a period of one hour. The locomotory activity of the animals is measured during the exploration phase, that is to say immediately after they are placed in the test cage.

DYSKINESIC SCORE

The dyskinesic score is determined according to a number of parameters and each with a different degree of intensity:

| PARA-METERS | DYSKINESIC SCORE | | | | |
|---|---|---|---|---|---|
| | 0 | 1 | 2 | 3 | 4 |
| Perch test | normal | slight | moderate | marked | severe |
| Climbing test | normal | slight | moderate | marked | severe |
| Paws (front, rear) | normal amplitude movement | small amplitude movement | large amplitude movement | | |
| Posture (back) | normal | moderate curvature | marked curvature | | |
| Jump | normal | uncoordinated | | | |
| Motility | normal | hyperactive | | | |
| Chorea | absent | present | | | |

-continued

| PARA- | DYSKINESIC SCORE | | | | |
|---|---|---|---|---|---|
| METERS | 0 | 1 | 2 | 3 | 4 |
| Dystonia | absent | present | | | |
| Expression | normal | repetitive | | | |
| Stereotyping | absent | present | | | |
| Orolingual movements | absent | present | | | |
| Vocalization | normal | for watching | for communicating | absent | |

This score is measured on days 57, 60, 67 and 104.

The evaluation is made 30 min or 2 h after the first daily injection of L-DOPA (4 h after the riluzole or sucrose solution).

The results are reported in Tables 1 to 5 and FIGS. 1, 2A, 2B and 3:

BRIEF DESCRIPTION OF THE DRAWINGS

Table 1 and FIG. 1 show that the acute administration of L-DOPA at a dose of 25 mg/kg, 15 days after the 3rd injection of MPTP, increases the locomotory activity by decreasing the small movements and increasing the large movements. These results therefore demonstrate that the acute administration of L-DOPA improves the locomotory activity.

Tables 2, 3 and 4

Figure 1:
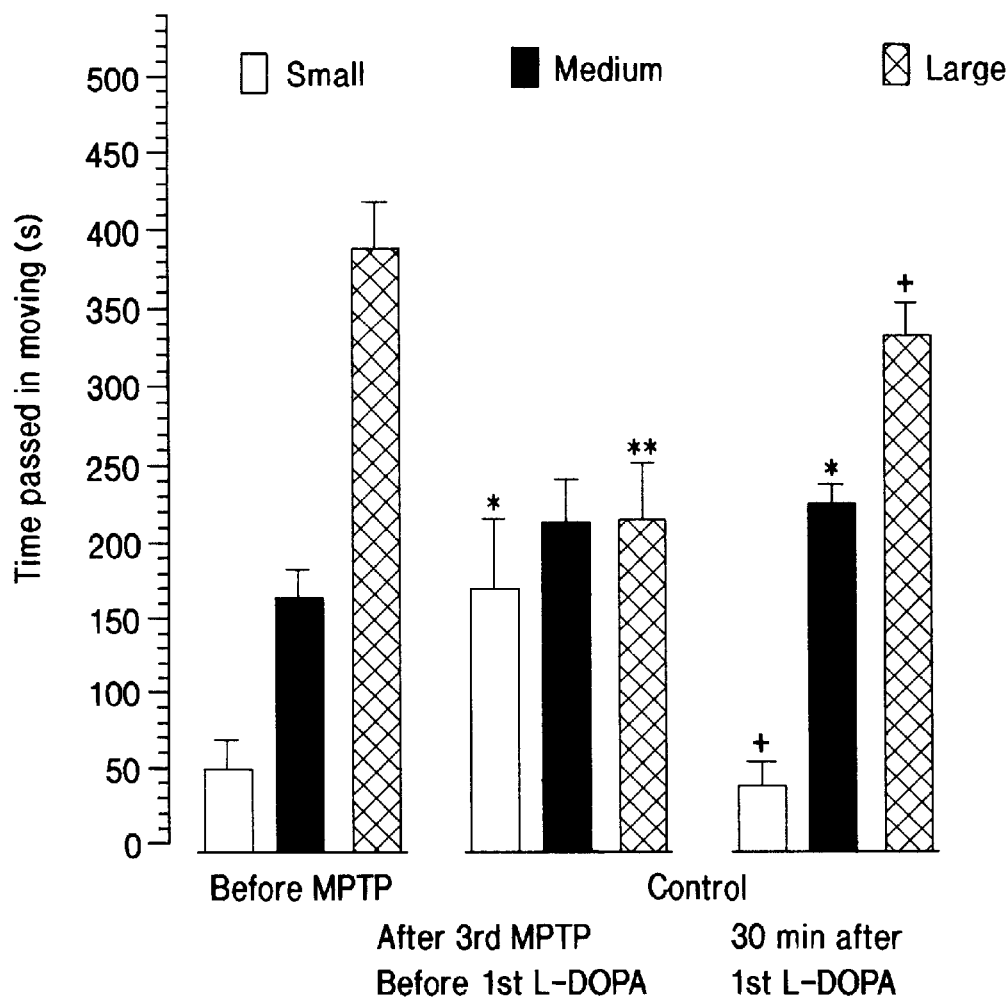
Figure 2A:
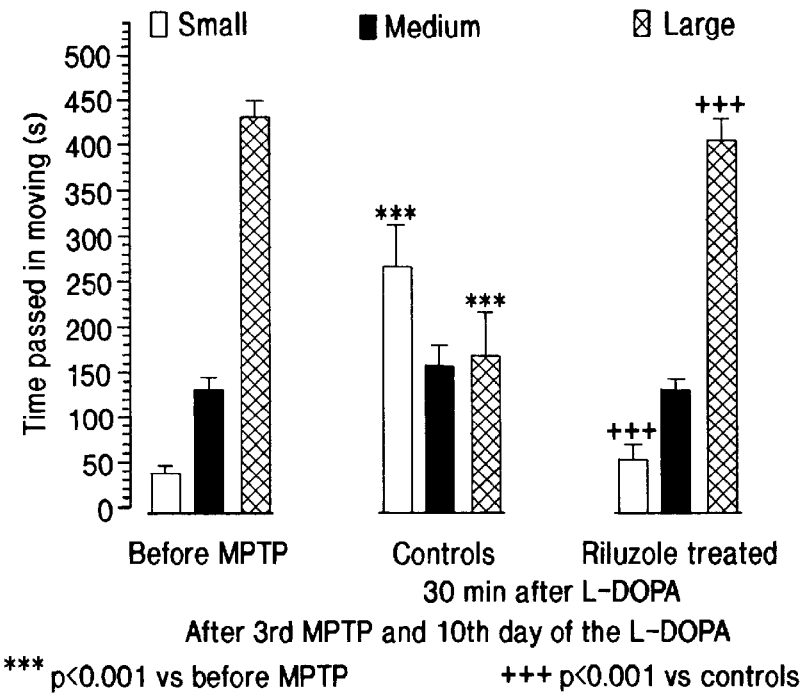
FIGS. 2A and 2B show that L-DOPA, after a repeated treatment of 10 days and of 20 days, does not have or has little beneficial effect on the locomotory activity of parkinsonian marmosets.
Figure 2B:
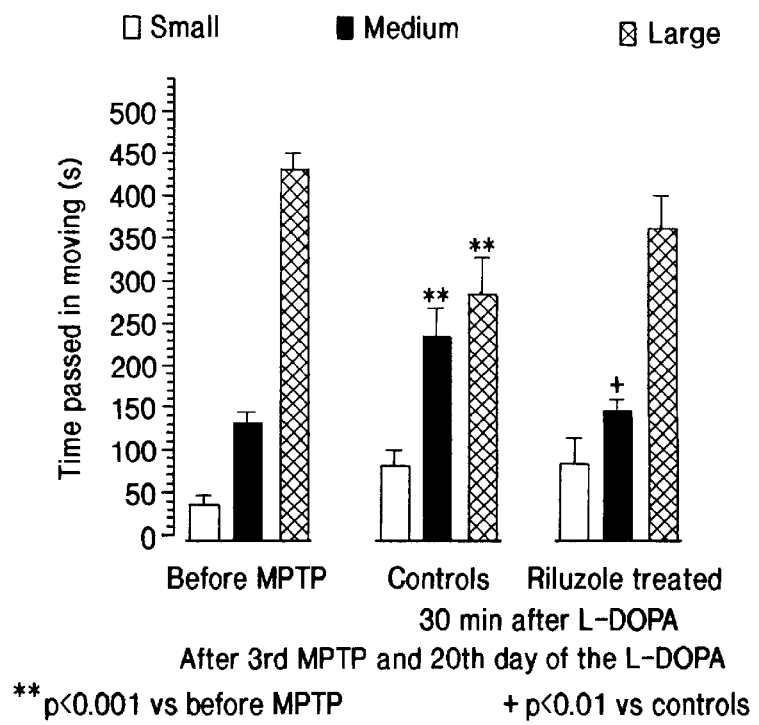

Tables 2, 3 and 4 and FIGS. 2A and 2B also show that riluzole at a dose of 10 mg/kg, by the oral route, twice per day for 72 days is capable of improving the locomotory activity and this is observed equally well after 10 days as after 20 days of treatment with L-DOPA.

Table 5 and FIG. 3 show that the repeated administrations of L-DOPA (25 mg/kg, by the oral route, 3 times per day) produce dyskinesias observed on days 57, 60, 67 and 104, with a maximum effect on day 104.

Table 5 and FIG. 3 also show that riluzole (at a dose of 10 mg/kg, by the oral route, twice per day) reduces the dyskinesias induced by L-DOPA and this is observed from day 57 to day 104.

TABLE 1

Effect of L-DOPA on the locomotory activity of parkinsoian marmosets

| Marmoset | Group 1 (sucrose) | | | | | | | | |
|---|---|---|---|---|---|---|---|---|---|
| No. | 1 | 2 | 3 | 1 | 2 | 3 | 1 | 2 | 3 |
| Class of movements | Time interval of measurements | before MPTP | | | before the 1st administration of L-DOPA | | | 30 min after the 1st administration of L-DOPA | | |
| Small movements | 1–10 | 290 | 15 | 10 | 90 | 175 | 50 | 5 | 305 | 20 |
| | 11–20 | 25 | 0 | 40 | 135 | 35 | 115 | 25 | 35 | 10 |
| | 21–30 | 215 | 20 | 5 | 85 | 95 | 485 | 5 | 20 | 0 |
| | 31–40 | 40 | 0 | 0 | 45 | 0 | 455 | 15 | 60 | 55 |
| | 41–50 | 60 | 35 | 0 | 45 | 5 | 560 | 45 | 15 | 10 |
| | 51–60 | 120 | 5 | 5 | 115 | 50 | 545 | 30 | 35 | 35 |
| | Average ± S.E.M. | 49 ± 19 | | | 171 ± 46 ± | | | 40 ± 16 ± | | |
| Medium movements | 1–10 | 140 | 185 | 60 | 255 | 285 | 375 | 235 | 270 | 250 |
| | 11–20 | 165 | 75 | 60 | 260 | 270 | 475 | 190 | 290 | 240 |
| | 21–30 | 200 | 245 | 165 | 275 | 175 | 75 | 225 | 205 | 110 |
| | 31–40 | 270 | 115 | 15 | 310 | 130 | 130 | 355 | 205 | 255 |
| | 41–50 | 270 | 265 | 125 | 280 | 95 | 40 | 260 | 165 | 165 |
| | 51–60 | 280 | 150 | 155 | 255 | 110 | 55 | 240 | 200 | 215 |
| | Average ± S.E.M. | 163 ± 19 | | | 214 ± 28 | | | 226 ± 13 * | | |
| Large movements | 1–10 | 175 | 405 | 535 | 260 | 145 | 180 | 365 | 30 | 335 |
| | 11–20 | 410 | 525 | 500 | 205 | 295 | 10 | 385 | 275 | 350 |
| | 21–30 | 185 | 335 | 430 | 240 | 330 | 40 | 370 | 375 | 490 |
| | 31–40 | 290 | 485 | 585 | 245 | 470 | 15 | 230 | 335 | 290 |
| | 41–50 | 270 | 300 | 475 | 275 | 500 | 0 | 295 | 420 | 425 |
| | 51–60 | 200 | 445 | 440 | 230 | 440 | 0 | 330 | 365 | 350 |
| | Average ± S.E.M. | 388 ± 30 | | | 216 ± 38 ** | | | 334 + 23 + | | |

Significant difference versus the value before MPTP: P<0.01 **P<0.001 (Student's test); significant difference versus the value before L-DQPA: +P<0.01 (Student's test)

TABLE 2

Effect of riluzole on the locomotory activity
in dyskinesic marmosets
Before MPTP

| Class of move-ments | Time interval of measurement (min) Marmoset No. | Time passed in moving | | | | | |
|---|---|---|---|---|---|---|---|
| | | Group 1 | | | Group 2 | | |
| | | 1 | 2 | 3 | 4 | 5 | 6 |
| Small move-ments | 1–10 | 290 | 15 | 10 | 35 | 10 | 5 |
| | 11–20 | 25 | 0 | 40 | 25 | 0 | 0 |
| | 21–30 | 215 | 20 | 5 | 70 | 25 | 40 |
| | 31–40 | 40 | 0 | 0 | 45 | 0 | 5 |
| | 41–50 | 60 | 35 | 0 | 105 | 0 | 10 |
| | 51–60 | 120 | 5 | 5 | 25 | 55 | 5 |
| | Average ± S.E.M. | | | 37 ± 10 | | | |
| Medium move-ments | 1–10 | 140 | 185 | 60 | 50 | 60 | 35 |
| | 11–20 | 165 | 75 | 60 | 45 | 85 | 35 |
| | 21–30 | 200 | 245 | 165 | 105 | 95 | 150 |
| | 31–40 | 270 | 115 | 15 | 80 | 60 | 80 |
| | 41–50 | 270 | 265 | 125 | 160 | 60 | 145 |
| | 51–60 | 280 | 150 | 155 | 245 | 215 | 95 |
| | Average ± S.E.M. | | | 132 ± 13 | | | |
| Large move-ments | 1–10 | 175 | 405 | 535 | 520 | 535 | 565 |
| | 11–20 | 410 | 525 | 500 | 530 | 515 | 565 |
| | 21–30 | 185 | 335 | 430 | 425 | 480 | 410 |
| | 31–40 | 290 | 485 | 585 | 475 | 540 | 515 |
| | 41–50 | 270 | 300 | 475 | 335 | 540 | 445 |
| | 51–60 | 200 | 445 | 440 | 330 | 330 | 500 |
| | Average ± S.E.M. | | | 432 ± 19 | | | |

TABLE 3

Effect of riluzole on the locomotory activity
in dyskinesic marmosets
10 days after L-DOPA

| Class of move-ments | Time interval of measurements (min) Marmoset No. | Time passed in moving (evaluated 30 min after the 1st daily administration of L-DOPA) | | | | | |
|---|---|---|---|---|---|---|---|
| | | Group 1 (sucrose) | | | Group 2 riluzole (2 × 10 mg/kg) | | |
| | | 1 | 2 | 3 | 4 | 5 | 6 |
| Small move-ments | 1–10 | 5 | 510 | 375 | 5 | 5 | 5 |
| | 11–20 | 0 | 500 | 295 | 0 | 5 | 45 |
| | 21–30 | 0 | 560 | 365 | 0 | 125 | 50 |
| | 31–40 | 10 | 485 | 370 | 0 | 145 | 25 |
| | 41–50 | 10 | 465 | 230 | 30 | 195 | 40 |
| | 51–60 | 205 | 225 | 240 | 35 | 210 | 100 |
| | Average ± S.E.M. | 269 ± 47*** | | | 57 ± 16+++ | | |
| Medium move-ments | 1–10 | 115 | 55 | 190 | 40 | 105 | 80 |
| | 11–20 | 70 | 70 | 295 | 35 | 140 | 185 |
| | 21–30 | 100 | 40 | 235 | 60 | 120 | 115 |
| | 31–40 | 155 | 35 | 175 | 140 | 215 | 190 |
| | 41–50 | 155 | 115 | 370 | 155 | 205 | 175 |
| | 51–60 | 165 | 305 | 235 | 135 | 125 | 190 |
| | Average ± S.E.M. | 160 ± 23 | | | 134 ± 13 | | |
| Large move-ments | 1–10 | 485 | 40 | 40 | 560 | 495 | 520 |
| | 11–20 | 530 | 30 | 10 | 565 | 455 | 370 |
| | 21–30 | 500 | 0 | 0 | 540 | 355 | 435 |
| | 31–40 | 435 | 80 | 55 | 460 | 240 | 385 |
| | 41–50 | 435 | 20 | 0 | 415 | 200 | 385 |
| | 51–60 | 230 | 70 | 125 | 430 | 265 | 310 |
| | Average ± S.E.M. | 171 ± 48*** | | | 410 ± 25+++ | | |

Significant difference versus value before MPTP: ***P<0.0001 (Student's test)
Significant difference versus control value: +++P<0.0001 (Student's test)

TABLE 4

Effect of riluzole on the locomotory acitivty
in dyskinesic marmosets
20 days after L-DOPA

| Class of move-ments | Time interval of measurements (min) Marinoset No. | Time passed in moving (evaluated 30 min after the 1st daily administration of L-DOPA) | | | | | |
|---|---|---|---|---|---|---|---|
| | | Group 1 (sucrose) | | | Group 2 riluzole (2 × 10 mg/kg) | | |
| | | 1 | 2 | 3 | 4 | 5 | 6 |
| Small move-ments | 1–10 | 105 | 5 | 45 | 5 | 130 | 35 |
| | 11–20 | 40 | 0 | 45 | 5 | 395 | 5 |
| | 21–30 | 120 | 10 | 105 | 0 | 170 | 20 |
| | 31–40 | 125 | 0 | 65 | 5 | 275 | 15 |
| | 41–50 | 130 | 15 | 265 | 0 | 135 | 15 |
| | 51–60 | 185 | 0 | 230 | 0 | 345 | 15 |
| | Average ± S.E.M. | 83 ± 19 | | | 67 ± 30 | | |
| Medium move-ments | 1–10 | 360 | 0 | 475 | 155 | 140 | 80 |
| | 11–20 | 260 | 20 | 475 | 255 | 160 | 105 |
| | 21–30 | 225 | 35 | 400 | 175 | 250 | 100 |
| | 31–40 | 325 | 55 | 300 | 180 | 175 | 80 |
| | 41–50 | 265 | 95 | 280 | 95 | 220 | 125 |
| | 51–60 | 315 | 30 | 315 | 90 | 180 | 105 |
| | Average ± S.E.M. | 235 ± 37** | | | 148 ± 13+ | | |
| Large move-ments | 1–10 | 140 | 600 | 85 | 445 | 335 | 490 |
| | 11–20 | 300 | 580 | 80 | 340 | 45 | 490 |
| | 21–30 | 255 | 555 | 95 | 425 | 180 | 480 |
| | 31–40 | 150 | 545 | 235 | 415 | 150 | 505 |
| | 41–50 | 205 | 490 | 55 | 505 | 245 | 460 |
| | 51–60 | 100 | 570 | 55 | 510 | 75 | 480 |
| | Average ± S.E.M. | 283 ± 50** | | | 365 ± 37 | | |

Significant difference versus value before MPTP: **P<0.001 (Student's test)
Significant difference versus control value: +p<0.01 (Student's test)

TABLE 5

Effect of riluzole on dyskinesic marmosets

| | Total dyskinesic score (evaluated 30 min after the 1st daily administration of L-DOPA) | | | | | |
|---|---|---|---|---|---|---|
| Day after the 1st | Group 1: controls (sucrose) | | | Group 2: riluzole (2 × 10 mg/kg p.o.) | | |
| injection of MPTP | Individual values | | | Individual values | | Average |
| Marmoset No. | 1 | 2 | 3 | ± S.E.M. | 4 | 5 | 6 | ± S.E.M. |
| 57 | 4 | 11 | 5 | 6.7 ± 2.1 | 3 | 3 | 1 | 2.3 ± 0.7 |
| 60 | 4 | 11 | 12 | 9.0 ± 2.5 | 3 | 3 | 1 | 2.3 ± 0.7[+] |
| 67 | 4 | 14 | 12 | 10 ± 3.0 | 3 | 3 | 1 | 2.3 ± 0.7[+] |
| 104 | 4 | 17 | 2 | 11 ± 3.8 | 1 | 3 | 3 | 2.3 ± 0.7[+] |

| | Total dyskinesic score (evaluated 2 h after the 1st daily administration of L-DOPA) | | | | | |
|---|---|---|---|---|---|---|
| Day after the 1st | Group 1: controls (sucrase) | | | Group 2: riluzole (2 × 10 mg/kg p.o.) | | |
| injection of MPMT | Individual values | | | Average | Individual values | | Average |
| Marmoset No. | 1 | 2 | 3 | ± S.E.M. | 4 | 5 | 6 | ± S.E.M. |
| 57 | 3 | 10 | 5 | 6.0 ± 2.1 | 3 | 3 | 0 | 2.0 ± 1.0 |
| 60 | 4 | 9 | 12 | 8.3 ± 2.32 | 2 | 3 | 1 | 2.0 ± 0.6[+] |
| 67 | 4 | 13 | 13 | 10 ± 3.0 | 3 | 3 | 1 | 2.3 ± G.7[+] |
| 104 | 5 | 17 | 12 | 11 ± 3.0 | 1 | 3 | 3 | 2.3 ± 0.7[+] |

Significant intergoup difference versus value of like control: [+]$P<0.05$ (Student's test)

In conclusion, these results demonstrate that, on the one hand, L-DOPA after an acute administration increased the locomotory activity by decreasing the small displacements, and by increasing the large displacements of the parkinsonian marmosets. On the contrary, L-DOPA, after a repeated treatment, not only produced little or no effect on locomotory activity, but in addition produced secondary effects, dyskinesias in parkinsonian marmosets.

On the other hand, these results show that in parkinsonian marmosets, riluzole improves the locomotory activity and prevents the development of dyskinesias induced by chronic treatment with L-DOPA. The combination riluzole and L-DOPA thus has a double beneficial effects in parkinsonian marmosets, by improving the locomotory activity and by decreasing the secondary effects, the dyskinesias, induced by L-DOPA.

Riluzole or one of its pharmaceutically acceptable salts and L-DOPA can be administered in the form of a combination and optionally combined with any other pharmaceutically compatible product, which can be inert or physiologically active.

Riluzole or one of its pharmaceutically acceptable salts and L-DOPA can likewise be administered separately or in a manner which is spread out in time so as to obtain the maximum efficacy.

Thus in the sense of the present invention, the combinations are not uniquely limited to those which are obtained by physical mixing of the constituents but also to those which allow a separate administration which can be simultaneous or spread out in time.

It is likewise possible to add to this combination a decarboxylase inhibitor such as benserazide or carbidopa.

In the combinations according to the invention, 10 to 400 parts by weight of riluzole are generally used per 100 to 6000 parts by weight of L-DOPA and, preferably, 200 to 4000 parts by weight of L-DOPA or the equivalent of this quantity when the L-DOPA is mixed with a decarboxylase inhibitor. Generally, the quantity of L-DOPA when this is mixed with an L-DOPA inhibitor is 50 to 1500 parts by weight.

When the decarboxylase inhibitor is benserazide, a quantity by weight thereof of 2 to 6 times less than the quantity of L-DOPA and more particularly 4 times less than the quantity of L-DOPA is generally used.

When the decarboxylase inhibitor is carbidopa, a quantity by weight thereof of 2 to 15 times less than the quantity of L-DOPA and more particularly 4 to 10 times less than the quantity of L-DOPA is generally used.

The combination can be employed by the oral, parenteral or rectal route.

Pharmaceutically acceptable salts of riluzole which can be especially mentioned are the addition salts with mineral acids such as the hydrochlorides, sulphates, nitrates, phosphates or organic acids such as the acetates, propionates, succinates, oxalates, benzoates, fumarates, maleates, methanesulphonates, isethionates, theophilline acetates, salicylates, phenolphthaleinates, methylene-bis-β-oxynaphthoates or of substitution derivatives of these derivatives.

Solid compositions for oral administration which can be used are compressed tablets, pills, powders (gelatin capsules, cachets) or granules. In these compositions, the active principles are mixed with one or more inert diluents, such as starch, cellulose, sucrose, lactose or silica, under a current of argon. These compositions can likewise comprise substances other than the diluents, for example one or more lubricants such as magnesium stearate or talc, a colourant, a coating (coated tablets) or a lacquer.

Liquid compositions for oral administration which can be used are solutions, suspensions, emulsions, syrups and pharmaceutically acceptable elixirs containing inert diluents such as water, ethanol, glycerol, vegetable oils or paraffin oil. These compositions can comprise substances other than the diluents, for example wetting, sweetening, thickening, aromatizing or stabilizing products.

The sterile compositions for parenteral administration can preferably be aqueous or non-aqueous solutions, suspensions or emulsions. As a solvent or vehicle, it is possible to employ water, propylene glycol, a polyethylene glycol, vegetable oils, in particular olive oil, injectable organic esters, for example ethyl oleate or other suitable organic solvents. These compositions can likewise contain adjuvants, in particular wetting, isotonicizing, emulsifying, dispersing and stabilizing agents. Sterilization can take place in several ways, for example by sterile filtration, by incorporating sterilizing agents in the composition, by irradiation or by heating. They can likewise be prepared in the form of sterile solid compositions which can be dissolved at the time of use in sterile water or any other sterile injectable medium.

The compositions for rectal administration are suppositories or rectal capsules which contain, apart from the active product, excipients such as cocoa butter, semisynthetic glycerides or polyethylene glycols.

The present invention likewise relates to the method of treatment of parkinsonian patients which consists in administering to the patient a L-DOPA and riluzole combination or one of its pharmaceutically acceptable salts and optionally a decarboxylase inhibitor either simultaneously or separately or in a manner which is spread out in time.

The doses depend on the effect sought, on the duration of treatment and on the route of administration used; they are generally from 10 to 400 mg per day by the oral route for an adult with unit doses ranging from 10 to 200 mg of riluzole and from 100 to 6000 mg and preferably 200 to 4000 mg per day by the oral route for an adult with unit doses of 100 to 250 mg of L-DOPA or the equivalent of this dose when the L-DOPA is administered with a decarboxylase inhibitor. Thus when the L-DOPA is administered with a decarboxylase inhibitor the dose of L-DOPA is generally from 50 to 1500 mg per day by the oral route.

When the decarboxylase inhibitor is benserazide, it is preferable to administer per day, by the oral route, for an adult, 10 to 400 mg of riluzole, 50 to 1500 mg of L-DOPA and a quantity of benserazide by weight which is 2 to 6 times less and particularly 4 times less than the quantity by weight of L-DOPA.

When the decarboxylase inhibitor is carbidopa, it is preferable to administer per day, by the oral route, for an adult, 10 and 400 mg of riluzole, 50 to 1500 mg of L-DOPA and a quantity of carbidopa by weight which is 2 to 15 times less and particularly 4 to 10 times less than the quantity by weight of L-DOPA.

Generally speaking, the physician will determine the appropriate dosage as a function of the age, the weight and all of the other factors peculiar to the subject to be treated.

What is claimed is:

1. A pharmaceutical composition comprising a combination of levodopa and riluzole or a pharmaceutically acceptable salt thereof.

2. The pharmaceutical composition as set forth in claim 1 which further comprises a decarboxylase inhibitor.

3. The pharmaceutical composition as set forth in claim 2 wherein the decarboxylase inhibitor is benserazide or carbidopa.

4. The pharmaceutical composition as set forth in claim 1 in which riluzole is present from about 10 parts to about 400 parts by weight and levodopa is present from about 100 parts to about 6000 parts by weight.

5. The pharmaceutical composition as set forth in claim 1 in which riluzole is present from about 10 parts to about 400 parts by weight and levodopa is present from about 200 parts to about 4000 parts by weight.

6. The pharmaceutical composition as set forth in claim 2 in which riluzole is present from about 10 parts to about 400 parts by weight and levodopa is present from about 50 parts to about 1500 parts by weight.

7. The pharmaceutical composition as set forth in claim 6 in which the decarboxylase inhibitor is benserazide.

8. The pharmaceutical composition as set forth in claim 6 in which the decarboxylase inhibitor is carbidopa.

9. The pharmaceutical composition as set forth in claim 1 which is administered to a patient in need thereof either simultaneously, separately or administered separately by spreading out in time.

10. The pharmaceutical composition as set forth in claim 2 which is administered to a patient in need thereof either simultaneously, separately or administered separately by spreading out in time.

11. The pharmaceutical composition as set forth in claim 5 which is administered to a patient in need thereof either simultaneously, separately or administered separately by spreading out in time.

12. The pharmaceutical composition as set forth in claim 7 which is administered to a patient in need thereof either simultaneously, separately or administered separately by spreading out in time.

13. The pharmaceutical composition as set forth in claim 8 which is administered to a patient in need thereof either simultaneously, separately or administered separately by spreading out in time.

14. The pharmaceutical composition as set forth in claim 1 useful in the treatment of Parkinson's disease.

15. The pharmaceutical composition as set forth in claim 2 useful in the treatment of Parkinson's disease.

16. The pharmaceutical composition as set forth in claim 5 useful in the treatment of Parkinson's disease.

17. The pharmaceutical composition as set forth in claim 7 useful in the treatment of Parkinson's disease.

18. The pharmaceutical composition as set forth in claim 8 useful in the treatment of Parkinson's disease.

19. A pharmaceutical compositions comprising riluzole useful as a medicament in the prevention and treatment of dyskinesias induced by levodopa.

20. A method of treating Parkinson's disease comprising administering to a patient in need thereof an effective amount of riluzole or a pharmaceutically acceptable salt thereof in combination with levodopa, optionally in combination with the pharmaceutically acceptable carrier.

* * * * *